(12) United States Patent
Campidelli et al.

(10) Patent No.: US 11,635,367 B2
(45) Date of Patent: Apr. 25, 2023

(54) CONTRAST-AMPLIFYING CARRIERS USING A TWO-DIMENSIONAL MATERIAL

(71) Applicants: COMMISSARIAT A L'ENERGIE ATOMIQUE ET AUX ENERGIES ALTERNATIVES, Paris (FR); CENTRE NATIONAL DE LA RECHERCHE SCIENTIFIQUE (CNRS), Paris (FR); UNIVERSITE DU MANS, Le Mans (FR)

(72) Inventors: Stéphane Campidelli, Saint Remy l'honore (FR); Renaud Cornut, Chatillon (FR); Vincent Derycke, Montigny-le-Bretonneux (FR); Dominique Ausserre, Soulitre (FR); Manuel Ausserre, Lyons (FR)

(73) Assignees: CENTRE NATIONAL DE LA RECHERCHE SCIENTIFIQUE (CNRS), Paris (FR); UNIVERSITE DU MANS, Le Mans (FR); COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 449 days.

(21) Appl. No.: 16/063,652

(22) PCT Filed: Dec. 16, 2016

(86) PCT No.: PCT/EP2016/081600
§ 371 (c)(1),
(2) Date: Jun. 18, 2018

(87) PCT Pub. No.: WO2017/103222
PCT Pub. Date: Jun. 22, 2017

(65) Prior Publication Data
US 2019/0003956 A1    Jan. 3, 2019

(30) Foreign Application Priority Data
Dec. 17, 2015    (FR) .......................... 1562668

(51) Int. Cl.
*G01N 21/01*        (2006.01)
*G01N 33/543*       (2006.01)
(Continued)

(52) U.S. Cl.
CPC ........... *G01N 21/01* (2013.01); *G01N 21/554* (2013.01); *G01N 21/6428* (2013.01);
(Continued)

(58) Field of Classification Search
CPC ............. G01N 21/01; G01N 33/54373; G01N 21/554; G01N 21/6428; G01N 21/658; G01N 33/54366; G02B 1/11
See application file for complete search history.

(56) References Cited

U.S. PATENT DOCUMENTS

2012/0116094 A1* 5/2012 Swager ................ C07D 303/38
548/256
2012/0199815 A1* 8/2012 Kondo .............. H01L 21/02527
257/29

(Continued)

FOREIGN PATENT DOCUMENTS

CN    203 217 962 U    9/2013
JP    2013-037779    * 2/2013

(Continued)

OTHER PUBLICATIONS

Azevedo, et al., "Versatile Wafer-Scale Technique for the Formation of Ultrasmooth and Thickness-Controlled Graphene Oxide Films Based on Very Large Flakes", ACS Appl Mater Interfaces, vol. 7, Issue 38, pp. 21270-21277, Sep. 8, 2015.

(Continued)

*Primary Examiner* — Melanie Brown
(74) *Attorney, Agent, or Firm* — BakerHostetler

(57) ABSTRACT

A contrast-amplifying carrier for observing a sample, includes a transparent substrate bearing at least one absor-
(Continued)

bent coating suitable for behaving as an antireflection coating when it is illuminated at normal incidence at an illumination wavelength λ through the substrate and when the face of the coating opposite the substrate is in contact with a medium referred to as a transparent ambient medium, the refractive index $n_3$ of which is lower than that of the refractive index $n_0$ of the substrate. The absorbent coating comprises: an absorbent sublayer referred to as the contrast sublayer, deposited on the surface of the transparent substrate; and an absorbent layer referred to as the sensitive layer, distinct from the contrast sublayer and comprising between 1 and 5 sheets of a graphene-type material. Methods for producing and for using such a contrast-amplifying carrier are also provided.

18 Claims, 3 Drawing Sheets

(51) Int. Cl.
*G02B 1/11* (2015.01)
*G01N 21/552* (2014.01)
*G01N 21/64* (2006.01)
*G01N 21/65* (2006.01)

(52) U.S. Cl.
CPC ..... *G01N 21/658* (2013.01); *G01N 33/54366* (2013.01); *G01N 33/54373* (2013.01); *G02B 1/11* (2013.01)

(56) References Cited

U.S. PATENT DOCUMENTS

| | | | |
|---|---|---|---|
| 2015/0064470 A1* | 3/2015 | Kimura | B32B 37/02 428/408 |
| 2015/0301039 A1 | 10/2015 | Arsenin et al. | |
| 2016/0299328 A1* | 10/2016 | Ausserre | G01N 33/54373 |
| 2016/0303838 A1* | 10/2016 | Chen | B32B 15/08 |
| 2017/0108362 A1* | 4/2017 | Engel | G01R 33/1269 |

FOREIGN PATENT DOCUMENTS

| | | | | |
|---|---|---|---|---|
| WO | 2011004136 A1 | 1/2011 | | |
| WO | WO 2015055809 | * | 4/2014 | ............ G01N 21/45 |
| WO | 2014/193819 A1 | 12/2014 | | |
| WO | 2015/055809 A1 | 4/2015 | | |
| WO | 2015055810 A1 | 4/2015 | | |

OTHER PUBLICATIONS

Shan, et al., "One-step transfer and doping of large area graphene by ultraviolet curing adhesive", Carbon, vol. 84, Apr. 1, 2015 (Apr. 1, 2015), pp. 9-13, XP029132036.
Ausserre, et al., "Absorbing Backside Anti-reflecting layers for high contrast imaging in fluid cells", May 29, 2014 (May 29, 2014), XP055146681.
Nguyen et al., "Surface Plasmon Resonance: A Versatile Technique for Biosensor Applications", Sensors, vol. 15, No. 5, May 5, 2015 (May 5, 2015), pp. 10481-10510, XP055264403.
Ausserre, et al., "Anti-Reflecting Absorbing Layers for Electrochemical and Biophotonic Applications", J Nanomed Nanotechnol, vol. 5, Issue 4, 2014.
Zhang, "Ultrathin Two-Dimensional Nanomaterials", ACS Nano, vol. 9, No. 10, pp. 9451-9469, (2015).
Chiu, et al., "Graphene Oxide Based Surface Plasmon Resonance Biosensors", Chapter 8, Advances in Graphene Science, InTech, 2013.
Bonaccorso et al., "Production and processing of graphene and 2d crystals", Materials Today, vol. 15, No. 12 pp. 564-589, (Dec. 2012).
Zamfir et al., "Synthesis and electroactivated addressing of ferrocenyl and azido-modified stem-loop oligonucleotides on an integrated electrochemical device", Electrochimica Acta 164, pp. 62-70, (2015).
Adjizian et al., "Dirac Cones in two-dimensional conjugated polymer networks", Nat. Commun., 5:5842, Dec. 18, 2014.
Azzam, and Bashara, "Ellipsometry and Polarized Light", North-Holland, 1987, p. 284.

\* cited by examiner

CONTRAST-AMPLIFYING CARRIERS USING A TWO-DIMENSIONAL MATERIAL

CROSS-REFERENCE TO RELATED APPLICATIONS

This application is a National Stage of International patent application PCT/EP2016/081600, filed on Dec. 16, 2016, which claims priority to foreign French patent application No. FR 1562668, filed on Dec. 17, 2015, the disclosures of which are incorporated by reference in their entirety.

FIELD OF THE INVENTION

The invention pertains to contrast-amplifying carriers for observing a sample, as well as to methods for producing such carriers. The invention also pertains to methods for observing samples and to methods for detecting or assaying chemical or biological species implementing such carriers.

BACKGROUND

The invention is suitable for application to various technical fields, such as biology (detecting biomolecules or microorganisms, observing individual cells or cell cultures), nanotechnologies (viewing nano-objects, such as nanotubes), microelectronics, materials science, etc.

The use of antireflection layers (or $\lambda/4$ layers) to increase the optical contrast of an object observed by reflecting optical microscopy is a highly potent technique that has been known for a number of years. Let I be the luminous intensity reflected by the object to be observed, deposited on a carrier, and $I_s$ that reflected by the carrier alone; then, the value of the contrast with which the sample is observed is $C=(I-I_s)/(I+I_s)$. It is understood that the absolute value of this contrast takes its maximum value (equal to 1) when $I_s=0$, i.e. when the carrier has a reflectivity of zero, or else when the carried object has a reflectivity of zero. In the simplest case, the condition $I_s=0$ is met by using, as the carrier, a transparent substrate on which a thin film, which is also transparent, is deposited, the thickness and the refractive index of which are suitably chosen. In the case of a single antireflection layer, illuminated at normal incidence with an incident medium (from which the illumination originates) and an emergent medium (the substrate), which are transparent and semi-infinite, the following conditions are obtained:

$$n_1^2 = n_0 n_3 \quad (1a)$$

$$n_1 e_1 = \lambda/4 \quad (1b)$$

where $n_1$ is the (real) refractive index of the layer, $n_0$ and $n_3$ are the (also real) refractive indices of the incident and emergent media, $e_1$ is the thickness of the layer and $\lambda$ the illumination wavelength.

For given incident and emergent media, equation (1a) unequivocally determines the refractive index of the antireflection layer. Unfortunately, this index may not correspond to a commonly used material, or to one meeting various requirements related to the specific application under consideration. For example, in the case of an air-glass interface, the practical interest of which is obvious, $n_1 \approx 1.27$ is obtained, which requires the use of composite materials such as aerogels.

To overcome this drawback, the use of absorbent antireflection layers has recently been proposed. See in this regard the international application WO2015/055809 and the following articles:

Ausserré D, Abou Khachfe R, Roussille L, Brotons G, Vonna L, et al. (2014) "Anti-Reflecting Absorbing Layers for Electrochemical and Biophotonic Applications" J Nanomed Nanotechnol 5: 214; and Ausserré D., Abou Khachfe R, Amra C., Zerrad M. "Absorbing Backside Anti-reflecting Layers for high contrast imaging in fluid cells." arXiv:1405.7672 [physics.optics].

This amounts to a genuine paradigm shift since, in the case of conventional $\lambda/4$ layers, the increase in contrast results from an interference effect that involves multiple reflections at the incident medium/layer and layer/emergent medium interfaces; however, the absorption of light within the layer tends to remove the interference between these multiple reflections: consequently, the very idea of an "absorbent antireflection layer" seems counterintuitive at first.

The use of an absorbent antireflection layer is advantageous since the additional degree of freedom associated with the presence of an imaginary part of the index allows the constraint bearing on the value of its real part to be relaxed. Additionally, while it is difficult to modify the real part of the refractive index of a material, it is relatively straightforward to modify its imaginary part (for example, by introducing absorbent or scattering impurities, scattering "simulating" absorption).

Furthermore, a contrast-amplifying carrier comprising an absorbent antireflection layer must be used in an "upside-down" or "back side" configuration, i.e. with illumination and observation through the substrate, which has a higher refractive index than that of the emergent medium (the "ambient medium"). This configuration is particularly suitable when the substrate forms an observation window and the absorbent antireflection layer is brought into contact with an aqueous medium (chemical or biological applications) or held in a vacuum chamber or under a controlled atmosphere (applications such as deposition processes).

The absorbent antireflection layers known from the prior art nonetheless exhibit a certain number of drawbacks.

First, despite the additional degree of freedom afforded to the designer through the use of a complex refractive index, it is difficult to produce "ideal" absorbent antireflection layers, i.e. those meeting both conditions required for complete reflection extinction.

Second, metal absorbent antireflection layers, which are particularly advantageous in principle, not least because they allow an electrical potential to be applied to the sample to be observed, are not perfectly smooth on the atomic scale. Additionally, when they are functionalized for chemical or biological detection applications, the distribution of ligands over their surface is not uniform. Furthermore, it is sometimes difficult to functionalize them, and this functionalization requires a different process depending on the choice of constituent material.

The aforementioned international application WO2015/055809 mentions the possibility of using graphene for producing an absorbent antireflection layer. However, to meet the conditions for reflection extinction on a fused glass or silica substrate, it would be necessary to use a layer comprising at least 8 to 10 graphene sheets. Unfortunately, it is very difficult to obtain such layers with a level of uniformity that is acceptable for the application under consideration, i.e. over an area greater than or equal to about 10 square micrometers.

SUMMARY OF THE INVENTION

The invention aims to overcome the aforementioned drawbacks of the absorbent antireflection layers known from the prior art.

According to the invention, this objective is achieved through the use of an absorbent antireflection coating comprising two distinct portions:

an absorbent sublayer, for example made of metal, referred to as the "contrast" sublayer, deposited on the surface of a transparent substrate; and a layer referred to as the "sensitive" layer comprising between 1 and 5 sheets of a two-dimensional material, in particular a graphene-type material, which may potentially be functionalized.

The sensitive layer, formed of several sheets of a two-dimensional material, for example a graphene-type material, makes it possible to obtain a smooth surface on the atomic scale and, in the case of functionalization, a uniform distribution of ligands. The contrast sublayer is needed to meet the conditions for reflection extinction, which would not be possible using only the sensitive layer. Furthermore, the composite structure of the coating according to the invention affords additional degrees of freedom, making it easier to obtain practically perfect reflection extinction.

It should be noted that the use of a layer of graphene, or of a graphene-type material, deposited on a metal layer has already been proposed in the context of surface plasmon resonance (SPR) sensors, see for example:

US 2015/0301039; and

Hoang Hiep Nguyen et al. "Surface Plasmon Resonance: A Versatile Technique for Biosensor Applications" Sensors 2015, 15, 10481-10510.

However, these sensors exploit a physical phenomenon that is entirely different from that on which the invention is based and require more restrictive operating conditions (illumination at highly oblique incidence and polarized light).

Thus, one subject of the invention is a contrast-amplifying carrier for observing a sample, comprising a transparent substrate bearing at least one absorbent coating suitable for behaving as an antireflection coating when it is illuminated at normal incidence at an illumination wavelength $\lambda$ through said substrate and when the face of said coating opposite said substrate is in contact with a medium referred to as a transparent ambient medium, the refractive index $n_3$ of which is lower than that of the refractive index $n_0$ of said substrate, characterized in that said absorbent coating comprises: an absorbent sublayer that is absorbent at said illumination wavelength $\lambda$ and which exhibits an antireflection behavior at this same wavelength, referred to as the contrast sublayer, deposited on the surface of said transparent substrate; and an absorbent layer referred to as the sensitive layer, distinct from said contrast sublayer and comprising between 1 and 5 sheets of at least one two-dimensional material.

Another subject of the invention is a method for producing such a contrast-amplifying carrier, said method comprising a phase of designing said carrier and a phase of physically producing the carrier thus designed.

Yet another subject of the invention is a method for observing a sample including the following steps:

A. placing said sample on the sensitive layer of such a contrast-amplifying carrier and bringing it into contact with a transparent ambient medium, the refractive index of which is lower than that of the substrate of said contrast-amplifying carrier;

B. illuminating said sample at normal incidence through said ambient medium, with an illumination cone including the normal incidence, with light radiation including at least one wavelength $\lambda$ such that the absorbent coating of said carrier behaves as an antireflection coating; and C. observing the sample thus illuminated, also through said ambient medium.

Yet another subject of the invention is a method for detecting or assaying at least one chemical or biological species or nanoparticles including the following steps:

I. providing such a contrast-amplifying carrier, comprising a functionalized sensitive layer that is capable of binding at least one chemical or biological species or nanoparticles;

II. bringing said functionalized surface or layer into contact with at least one solution containing a chemical or biological species that is capable of binding to said functionalized surface or layer, said solution being substantially transparent and exhibiting a refractive index that is lower than that of the substrate of said contrast-amplifying carrier;

III. illuminating said sample at normal incidence through said ambient medium at an illumination wavelength $\lambda$ such that the absorbent coating of said carrier behaves as an antireflection coating; and IV. observing said contrast-amplifying carrier thus illuminated, also through said substrate.

BRIEF DESCRIPTION OF THE DRAWINGS

Other features, details and advantages of the invention will become apparent upon reading the description provided with reference to the appended drawings, which are given by way of example and in which, respectively.

DETAILED DESCRIPTION

The figures are not to scale. In particular the thickness of certain layers (and in particular the sensitive layer made of a graphite-type material) has been greatly enlarged for the sake of clarity.

Hereinafter:

the term "two-dimensional material" will refer to a material taking the form of a single sheet of monatomic or monomolecular thickness, or of a stack of a small number (at most 10) of such sheets, potentially of different natures; a two-dimensional material may be crystalline or amorphous. Examples of two-dimensional materials are graphene and graphene-type materials (see below) as well as other materials of different chemical nature such as $WS_2$, $MoS_2$, $WSe_2$, conductive two-dimensional polymers, etc. See in particular the article by Hua Zhang "Ultrathin Two-Dimensional Nanomaterials", ACS Nano, Vol. 9, No. 10, 9451-9469 (2015) and, more specifically for conductive two-dimensional polymers, the article by J-J. Adjizian et al. "Dirac Cones in two-dimensional conjugated polymer networks" Nat. Commun. 5:5842 Dec. 18, 2014.

"graphene", unless further specified, will refer to a single sheet (i.e. a layer of monatomic thickness) of pure carbon, forming a hexagonal lattice;

a "graphene-type material" (or "graphene-related material", GRM) will refer to pure graphene, to a single sheet of a material derived from graphene such as graphene oxide, reduced graphene oxide, graphene doped by substituting certain carbon atoms with other atoms, graphane, graphyne, etc.; or to a stack of a small number (at most 10) of such sheets, potentially of different natures. Graphene oxide is particularly advantageous because it can be handled easily in solution, because it is "naturally" functionalized with a high density of epoxy, carboxyl and hydroxyl groups and because it lends itself particularly well to all sorts of surface functionalizations, for example by attaching amine groups to the carboxylic groups. See in this regard the article by Nan-Fu Chiu et al. "Graphene Oxide Based Surface Plasmon Resonance Biosensors", Chapter 8 of "Advances in Graphene Science", InTech, 2013;

a material will be considered absorbent at a wavelength $\lambda$ when the imaginary part of its refractive index at this wavelength is greater than or equal to 0.0001, preferably than 0.001, and more preferably still than 0.01. In the opposite case, it will be considered transparent. Using this definition, for example, all of the TCOs (transparent conducting oxides) are transparent.

Figure 1:
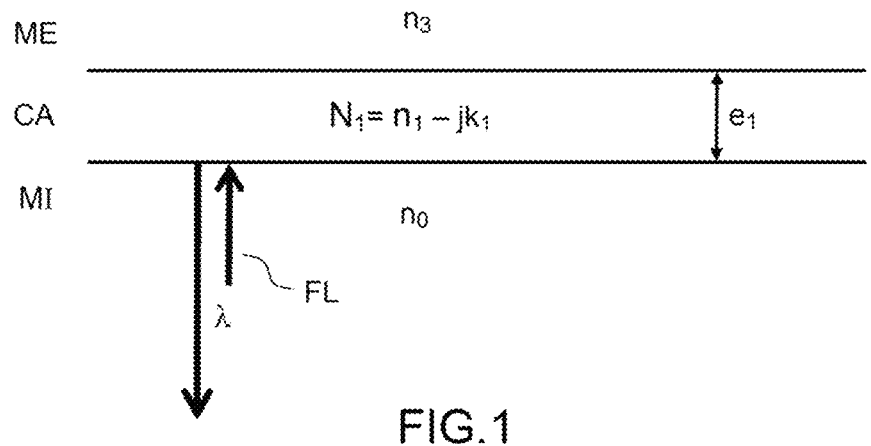
FIG. 1 illustrates the operating principle of an absorbent antireflection layer according to the prior art.

FIG. 1 presents an opportunity to recall the theory of absorbent antireflection layers, as already explained in the aforementioned international application WO2015/055809. It illustrates a beam of parallel light FL (which may be locally likened to a plane wave) that is monochromatic at a wavelength (in vacuum) $\lambda$, at normal incidence on a structure consisting of: a semi-infinite medium referred to as the incident medium MI, from which the light beam originates, which is transparent and characterized by a real refractive index $n_0$; an absorbent layer CA of thickness $e_1$, characterized by a complex refractive index $N_1=n_1-jk_1$ ("j" being the imaginary unit); and a semi-infinite medium referred to as the emergent medium, or ambient medium, ME, located of the side of the layer opposite that from which the light originates, which is transparent and characterized by a real refractive index $n_3<n_0$. The incident medium may in particular be a substrate, for example made of glass, on which the layer CA is deposited. A sample (not shown) having a real refractive index $n_2$, or having a complex refractive index $N_2=n_2-jk_2$, may be deposited on the layer CA, on the emergent medium side. As explained above, to maximize the contrast with which the sample is observed, it is necessary to eliminate the reflectance of the incident medium MI/layer CA/emergent medium ME assembly in the absence of a sample.

The complex reflection coefficient of a structure of the type illustrated in FIG. 1 (layer of thickness $e_1$ comprised between two semi-infinite media) is given by the Airy formula:

$$r_{013} = \frac{r_{01} + r_{13}e^{-2j\beta_1}}{1 + r_{01}r_{13}e^{-2j\beta_1}} \quad (2)$$

where $r_{ij}$ is the Fresnel coefficient at the i-j interface (i,j=0, 1 or 3, "0" corresponding to the incident medium, "1" to the layer CA and "3" to the emergent medium) and $\beta_1=2\pi n_1 e_1 \cos\theta_1/\lambda$ is the phase factor associated with said layer, $\theta_1$ being the angle of refraction in the layer. In a first instance, a transparent layer having a real index $n_1$ is considered, the generalization to the case of an absorbent layer being dealt with below. Still in a first instance, an incidence which may not be normal is considered.

The Fresnel coefficients for the "p" (TM) and "s" (TE) polarizations are:

$$r_{ij}^{(p)} = \frac{(n_j \cos\theta_i - n_i \cos\theta_j)}{(n_j \cos\theta_i + n_i \cos\theta_j)}$$

and $$r_{ij}^{(s)} = \frac{(n_i \cos\theta_i - n_j \cos\theta_j)}{(n_i \cos\theta_i + n_j \cos\theta_j)}$$

The antireflection condition corresponds to $r_{013}=0$ which, in the case of transparent media (real indices) gives two families of solutions:

the layers referred to as "$\lambda/2$" layers, for which $$e_1 = \frac{m\lambda}{(2n_1\cos\theta_1)}$$

where m is an integer, which exist only if $n_0=n_3$; and
the layers referred to as "$\lambda/4$", for which $$n_1 e_1 = (2p+1)\frac{\lambda}{4}$$

(p being an integer).

In the case in which the medium 1 (layer CA) is absorbent, its refractive index $N_1=n_1-jk_1$ is complex; the angle of refraction—which is then denoted by $\Theta_1$—and the phase coefficient—$B_1$—are also complex. In this case, $r_{013}=0$ dictates: $r_{01,s} \cdot r_{13,p} = r_{01,p} \cdot r_{13,s}$; this equality can only hold if one of the three following conditions: $\Theta_1=0$ (normal incidence), $N_1^2=n_0^2$ (no layer) or $n_0^2=n_3^2$ (identical incident and emergent media) is met. Consequently, in the case of any extreme media, the antireflection condition can be met only at normal incidence. Knowing that $r_{011,p}=-r_{01,s}$ and $r_{13,p}=-r_{13,s}$, equation (2) becomes:

$$N_1^2 - j\frac{(n_3-n_0)}{\tan B_1}N_1 - n_0 n_3 = 0 \quad (3)$$

Equation (3) is transcendental and it has no closed-form solution. However, solutions corresponding to the extreme cases may be found: namely that of a strongly absorbent layer and that of a weakly absorbent layer.

In the strongly absorbent case, it can be assumed that $e_1 \ll \lambda$ since light would not propagate through a very absorbent and thick layer; consequently, $|B_1| \ll 1$ and it is then possible to write, to the second order in $B_1$: $\tan B_1 \approx B_1 = \sqrt{n_3/n_0}(N_1/\sqrt{n_0 n_3})\delta_1$, where $\delta_1=(2\pi n_0/\lambda)e_1$. It is useful to separate the real and imaginary parts of the equation, and to use the "reduced" variables $\nu_1=n_1/\sqrt{n_0 n_3}$ and $\kappa_1=k_1/\sqrt{n_0 n_3}$. Equation (3) can then be written in the form of the following system:

$$\nu_1^2 - 1 + \kappa_1^2 \quad (4a)$$

$$\delta_1 = \frac{\left(\frac{n_0}{n_3}-1\right)}{2\nu_1 \kappa_1} \quad (4b)$$

Given that $\delta_1$ must be real and positive, there is the condition $n_0 > n_3$ ("reversed geometry"). By taking $n_0=1.52$ and $n_3=1.34$—this corresponding to the glass/water case customarily used in biophotonics—a thickness $e_1=(\lambda/2\pi)(n_0-n_3)/2n_1k_1$ of the order of a nanometer is found, thus confirming the initial assumption. It is interesting—and unexpected—that equation (4a) should tend toward the conventional index condition as $\kappa_1$—and therefore $k_1$—tends toward zero. A comparison with numerical results makes it possible to verify that equation (4a), although derived under the assumption of a strongly absorbent layer, is approximately valid for any value of $k_1$. However, the value of $e_1$ obtained from equation (4b) does not tend toward $\lambda/4n_1$, consequently, equation (4b) does not have general validity.

In the weakly absorbent case, let $B_1=\pi/2-\varepsilon_1$ (where $\varepsilon_1$ is a complex variable), thus implying:

$$\varepsilon_1 = \pi/2 - \sqrt{\frac{n_3}{n_0}}(v_1 - j\kappa_1)\delta_1.$$

It is then possible to write, to the second order in $\kappa_1$:

$$v_1^2 = 1 + \frac{\pi}{2}\sqrt{\frac{n_3}{n_0}}\left(\frac{n_0}{n_3}-1\right)\kappa_1 - 3\kappa_1^2 + o(\kappa_1^3) \quad (5a)$$

$$\delta_1 \simeq \frac{\pi}{2}\sqrt{\frac{n_0}{n_3}}\frac{1}{v_1}\left\{1 - \frac{4}{\pi}\frac{\sqrt{n_0/n_3}}{(n_0/n_3-1)}\kappa_1 + \kappa_1^2 + o(\kappa_1^3)\right\} \quad (5b)$$

In practice, equation (5a)—the domain of validity of which has proven to be very limited—is of little interest since, as mentioned above, equation (4a) constitutes a satisfactory approximation for any value of $\kappa_1$. By calculating the numerical solution to equation 3 it may be seen that the solution obtained for high $\kappa_1$ does not constitute an acceptable approximation $\kappa 1$ for low $\kappa_1$. However, there exists a semi-empirical equation which has proven to be satisfactory in all cases and which is given by equation 6b below. Equation 6a is simply equation 4a which, as was shown above, can be considered general and used as a replacement for 5b even for low $\kappa_1$:

$$v_1^2 = 1 + \kappa_1^2 \quad (6a)$$

$$\delta_1 \cong \frac{(n_0/n_3-1)}{2v_1\kappa_1}\left[1 - e^{-\frac{\kappa_1}{K}}\right] \quad (6b)$$

where $K=\{[\pi/(n_0/n_3-1)]\sqrt{n_0/n_3}\}^{-1}$

In practice, while being less restrictive than condition 1a that applies to transparent antireflection layers, condition 6a is still very restrictive. In practice, it is often possible to settle for meeting condition 6b in an approximate manner. In the case in which the contrast sublayer is made of a relatively unabsorbent material ($k_1<0.15$), the tolerance for $e_1$ could be of the order of $\lambda/100$, $\lambda/50$, $\lambda/20$ or $\lambda/10$, or even $\lambda/5$; in terms of $e_1$ this means a tolerance of the order of 0.01, 0.02, 0.05 or 0.1 or even 0.2. The tolerance for $e_1$ could be much higher in the case in which the contrast sublayer is made of a material that may be considered highly absorbent ($k_1>0.15$). In this case, it could reach 0.3 or even 0.6, although it will preferably be of the order of 0.1 or even 0.01.

It is therefore particularly useful to introduce a hierarchy between conditions 6a and 6b, which is explained by the following analysis:

The destructive interference between the beams reflected by the two surfaces f of an absorbent antireflection layer results from two contributions:

i) the amplitude of the reflection coefficients of these two surfaces;

ii) the phase shift between the beams reflected by the two surfaces, to which the difference in phase shift on reflection by each of the two surfaces and the optical path separating them contributes.

Equation 6a reflects the fact that the amplitude of the reflection coefficients is identical. Equation 6b reflects the fact that the emergent beams are in phase opposition.

If both equations are satisfied at the same time, extinction is total.

If only equation 6a is satisfied, the fluctuations in the intensity reflected by the layer with its thickness are maximum, which guarantees the possibility of perfect extinction, but which does not guarantee extinction, not even satisfactory extinction.

If only equation 6b is satisfied, extinction is not necessarily perfect, since the amplitudes reflected by the two surfaces may be different, but the thickness of the layer is such that extinction is satisfactory due to the optical path being adjusted so that these two reflections are in phase opposition, or "nearly" in phase opposition. It could be referred to as a antiresonant layer in this case. The term "nearly" reflects the fact that the differences in condition 6a affect the phases of the amplitudes reflected by the two surfaces, but that they affect them only slightly. It is for this reason that it is more important to approach condition 6b than to approach condition 6a. In practice, the index $N_1=n_1-jk_1$ varies substantially with wavelength and the product $v_1\kappa_1$ is subject to a period [p1, p2]. It is therefore necessary to choose the target wavelength for which the thickness of the layer is optimized. The variations in the product $v_1\kappa_1$ with wavelength are enough, through the choice of working wavelength, to make up for the error in the thickness by using equation 6b with the target wavelength when equation 6a is not satisfied.

It is therefore particularly judicious:

i) to approach condition 6a as far as possible (for example with a tolerance lower than or equal to 20%, preferably lower than or equal to 5%, and more preferably still lower than or equal to 1%, for $n_1$ and $k_1$, but it will sometimes be necessary to accept higher tolerances) taking into account the constraints imposed on the materials;

ii) to select a target wavelength such that the corresponding product $v_1\kappa_1$ is located toward the middle of the period [p1, p2];

iii) to determine $\delta_1$ by means of equation 6b applied to this target wavelength;

iv) to select the working wavelength that provides the best extinction.

In the case of a contrast sublayer, and with a view to obtaining even higher sensitivity, it might be advantageous to select a sublayer thickness that is less than the ideal thickness given by equation 6b, for example half of this thickness. It could be referred to as a sub-antiresonant sublayer in this case.

Lastly, it is worth specifying that the antireflection conditions described by equations 6a and 6b, which relate to normal incidence, also make it possible to obtain very low reflectivity for large illumination angles (for example up to a half-angle of 60°) and above all for observation, so much so that they allow highly sensitive imaging at high optical resolution.

Figure 2A:
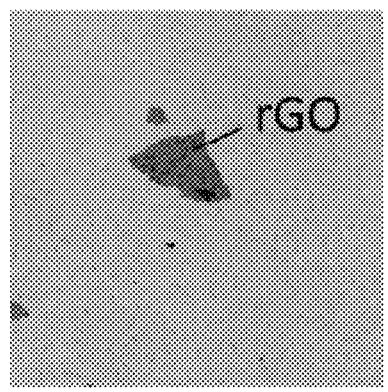
FIGS. 2A, 2B and 2C show experimental results demonstrating the feasibility of the invention and the real nature of its technical effect.
Figure 2B:
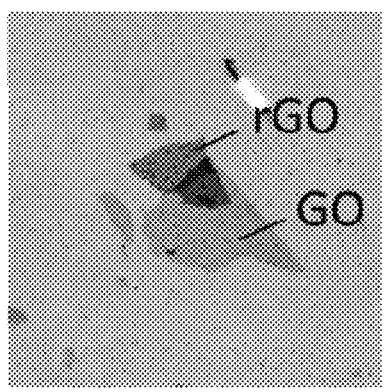
Figure 2C:
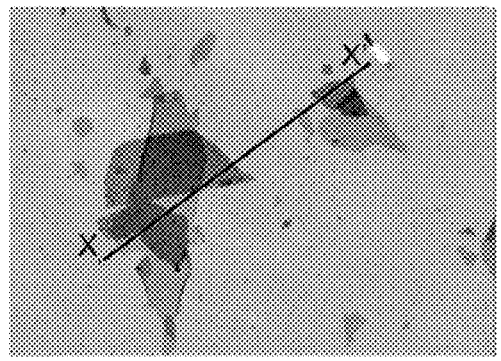

The inventors became aware that the performance of a nonideal absorbent antireflection layer, i.e. one completely or nearly meeting condition 6b (an "antiresonant" layer) but not condition 6a, for example made of metal, could be enhanced by depositing a small number (between 1 and 5) sheets of a graphene-type material on top thereof. This is illustrated by FIGS. 2A to 2C, which show sheets of graphene oxide (GO) and reduced graphene oxide (rGO) on an "optimal" absorbent antireflection layer made of Cr/Au on a glass substrate. The observation is made under the conditions of FIG. 1; it can be seen that the GO- or rGO-covered regions appear darker than those that are uncovered (negative contrast); this indicates that the presence of a graphene-type material makes it possible to get even closer to a condition for reflection extinction than what is possible using only a metal layer.

The invention makes use of this discovery, by proposing an absorbent antireflection coating comprising an "antiresonant" or "sub-antiresonant" absorbent sublayer made of a material other than a two-dimensional material, supporting a surface layer made of a two-dimensional material, and in particular a graphene-type material. As mentioned above, this makes it possible both to obtain better reflection extinction and to benefit from the excellent physical and chemical properties of graphene-type materials, or of other two-dimensional materials, the exclusive use of which for producing absorbent antireflection layers has proven to be troublesome.

Advantageously, an absorbent sublayer according to the invention exhibits an antireflection behavior that is close to optimal, with a reflectivity at normal incidence that is lower than or equal to 1%, preferably lower than or equal to 0.5% and more preferably still lower than or equal to 0.1% or even 0.05% at the target wavelength (or more generally one wavelength of the spectral band of the illumination) $\lambda$. Furthermore, its transmission coefficient at normal incidence will preferably be higher than or equal to 80%, preferably 85%, and more preferably still 90%, which may be obtained, in particular, by virtue of a low thickness, advantageously lower than or equal to 10 nm.

Figure 3:
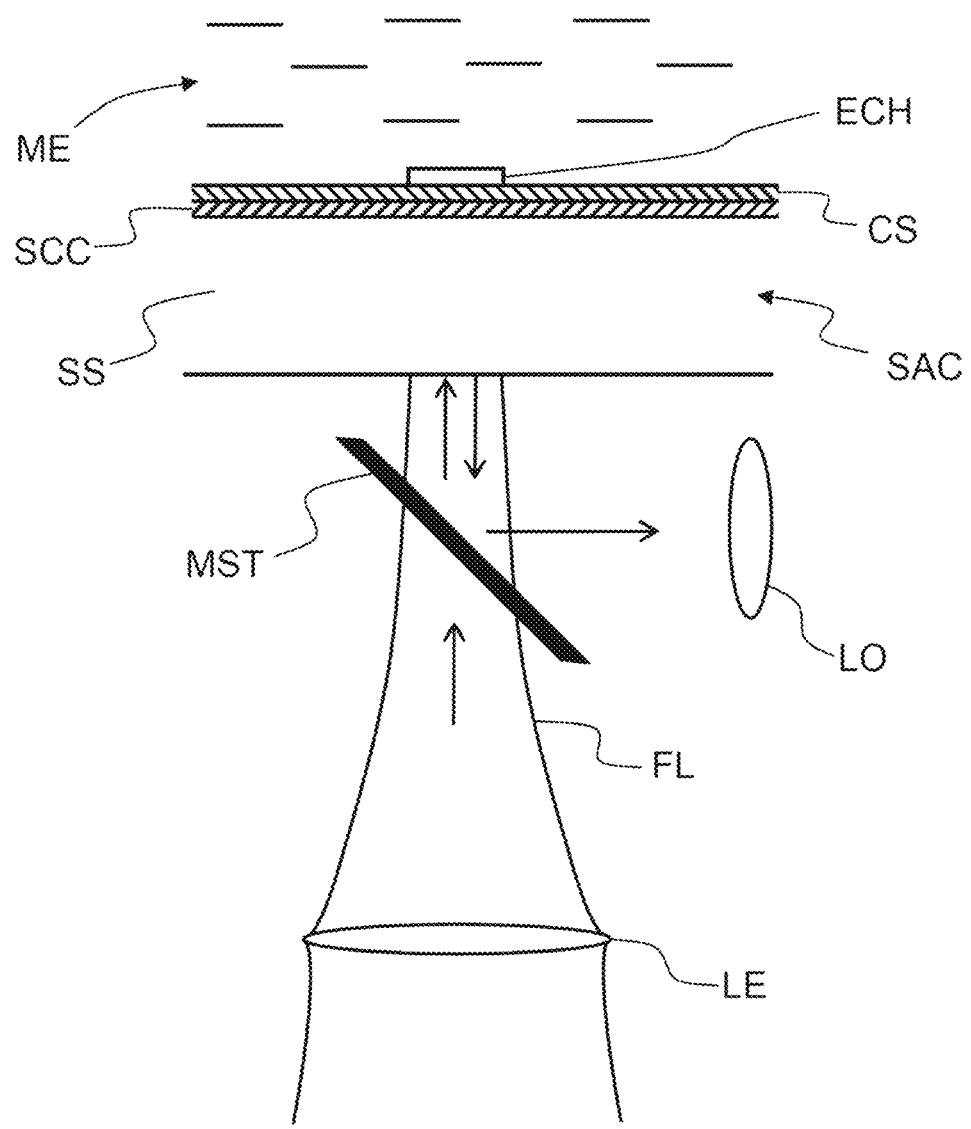
FIG. 3 shows a contrast-amplifying carrier using an absorbent antireflection layer according to one embodiment of the invention.

FIG. 3 shows a contrast-amplify carrier SAC comprising a transparent substrate SS, for example made of glass or of transparent plastic such as a polycarbonate or a polystyrene, serving as the incident medium, an antireflection absorbent sublayer SCC, referred to as the contrast sublayer (the structure of which may in fact be composite, in particular consist of a multilayer stack), deposited on said substrate, an absorbent layer CS made of a graphene-type material, referred to as the sensitive layer, deposited on the contrast sublayer and in contact with an emergent medium, or ambient medium, ME, for example an aqueous solution or air. A sample ECH is placed on a portion of the sensitive layer CS, on the emergent medium side. The substrate is illuminated at normal incidence by a light beam FL which is, in the example under consideration here, a Gaussian laser beam, focused by a lens LE onto the antireflection layer. It is in effect known that, in its focal region (beam waist), a Gaussian beam exhibits a planar phase front, and therefore may be locally likened to a plane wave (which case is considered in the theoretical discussions above). A semi-transparent mirror MST diverts a portion of the light reflected by the substrate SS/contrast sublayer SCC/sensitive layer CS/Sample ECH/emergent medium ME assembly, to direct it toward an objective LO, allowing said sample to be observed. In this configuration, the use of a diffusing disk rotating on the incident laser beam allows speckle-type parasitic interference to be removed. Observation may be performed by scanning, in particular using a confocal or "full-field" microscopy device. As a variant, it is possible to use a wide beam of parallel light for the illumination and to observe the intensity or color modulations over the cross section of the reflected beam or through imagery by means of a telecentric vision system. In the majority of cases an illumination cone having a half-angle potentially reaching 60°, but typically of the order of 20° to 30° or less, centered around the direction of normal incidence or in any case including this direction, will be used.

It should be noted that the spatial coherence of the incident light and its polarization state are of no importance; the illumination will therefore typically not be polarized. However, if it is desired to observe and/or to measure an intensity contrast, narrowband illumination should be used, or illumination consisting of multiple disjunct narrow spectral bands; polychromatic illumination resulting in a contrast which is a color rather than intensity contrast (the sample being observed with a different color than that of the background and different colors according to the thickness or the index of the sample).

In the setup of FIG. 3, the lenses LO and LE are interchangeable. Moreover, the parasitic reflection on the front face of the substrate can be usefully attenuated by techniques such as: immersion in an oil, the presence of a bevel between the front face and the rear face, spatial filtering, and conventional antireflection treatment.

The contrast-amplifying carrier according to the invention may also be used in fluorescence or Raman scattering microscopy. In this case, its antireflection properties are used to attenuate to a high degree reflection at the illumination wavelength so as to facilitate the detection of the less intense fluorescence or Raman scattering radiation.

To design a contrast-amplifying carrier of the type illustrated in FIG. 3, the following operations are performed:

First, a first material intended to form the substrate and a material intended to form the "ambient" or "emergent" medium are chosen. Typically, the choice of ambient medium is determined by the application under consideration (generally an aqueous solution for biological applications); the choice of material forming the substrate is dictated by technological considerations and by the constraint $n_3 < n_0$ at the wavelength $\lambda$ used for illumination and/or observation. Typically, a transparent plastic or glass substrate will be chosen, along with an ambient medium consisting of air ($n_3/n_0$ ratio comprised between 1.45 and 1.7) or water ($n_3/n_0$ ratio comprised between 1.1 and 1.3).

Second, the illumination wavelength (or the shortest illumination wavelength, if the illumination is polychromatic) $\lambda$ is determined according to the application under consideration or various technology constraints.

Third, equation 6a is used to determine the relationship linking the real part and the imaginary part of the refractive index of the constituent material of the contrast sublayer. A material approximately satisfying this relationship is then chosen or designed. For example, a transparent starting material may be chosen according to various technological considerations: for example a polymer, taking the real part of its refractive index as an imposed value, and modifying the imaginary part of said refractive index by adding impurities (dyes, nanoparticles, etc.) so as to get as close as possible to equation 6a.

Next, the thickness of said sublayer is determined by applying equation 6b (or either of equations 4b and 5b, which constitute particular cases thereof).

A two-dimensional material is then chosen, for example a graphene-type material, which is intended to form the sensitive layer. The choice may be dictated by various considerations, namely optical (maximizing reflection extinction, potentially with the aid of numerical simulations) and/or physicochemical (obtaining a smooth surface on the atomic scale and/or a particular interaction with the sample) considerations. The sensitive layer may in particular be functionalized, i.e. it may bear molecules (ligands) that are capable of binding certain chemical or biological species.

Next, the carrier is produced using conventional techniques, such as spin coating, or coating by immersion, rolling, sedimentation, or evaporation; physical or chemical vapor deposition, ion implantation, electrodeposition, Langmuir-Blodgett transfer, or bubbling method (J. Azevedo et al. "Versatile Wafer-Scale Technique for the Formation of Ultrasmooth and Thickness-Controlled Graphene Oxide Films Based on Very Large Flakes", ACS Appl Mater Interfaces. 2015 Sep. 30; 7(38):21270-7), etc.

The contrast sublayer may be made of metal (and in particular of gold), of a semiconductor, of a nonmetal conductor, of a polymer containing pigments or dyes, of an inorganic (mineral) material containing color centers, etc. Among the semiconductor materials suitable for producing absorbent antireflection layers are: germanium (for near-ultraviolet (UV) applications, for example at 354 nm), $TiO_2$ (also in the near-UV), molybdenum silicide, nickel silicide or titanium silicide (in the visible spectrum), tungsten silicide (in the near-infrared or in the near-UV), zirconium silicide (in the visible spectrum or in the near-UV) tantalum or vanadium (in the visible spectrum), etc. It may also contain metal nanoparticles. It may be magnetic, which is advantageous for studying samples which are themselves magnetic. The use of conductive layers, whether metal or not, makes it possible to apply a controlled potential difference to the sample and/or to carry out "electrochemical imaging" allowing electrodeposition, corrosion, catalysis, etc. phenomena to be studied and/or the ligands of the functionalized sensitive layer to be activated/deactivated. One particularly advantageous variant consists in producing a monolithic carrier, wherein the sublayer is a layer of implanted impurities, for example implanted by low-energy ion implantation, in the surface of the substrate. Although qualified as "absorbent", the contrast sublayer does not necessarily have to be absorbent in the strict sense: as a variant, it may be a scattering layer, the scattering "imitating" absorption and potentially also being modelled by a complex refractive index. Additionally, the contrast sublayer may be formed of a stack of elementary layers. Lastly, it may be advantageous for the contrast sublayer itself to be functionalized, for example by a layer of mercaptooctanoic acid $(O_8H_{16}O_2S)$ in the case in which it is a layer of gold (see in this regard the aforementioned article by Hua Zhang).

Numerous techniques make it possible to fabricate the sensitive layer of graphene-type material, such as chemical vapor deposition (CVD), molecular beam epitaxy (MBE) and liquid phase techniques. See for example F. Bonaccorso et al. "Production and processing of graphene and 2d crystals" Materials Today, Vol. 15, n° 12 (December 2012), pages 564-589.

The sensitive layer may be formed of a stack of sheets of the same or different type.

A contrast-amplifying carrier such as described above, having a functionalized sensitive layer, makes it possible to produce biochips for detecting and/or assaying chemical or biological species or nanoparticles, or even nanoparticles which are themselves carrying chemical or biological species to be detected that were captured by the nanoparticles in a prior step. In this application, the use of infrared or ultraviolet illumination is particularly advantageous. Specifically, the majority of captured species have absorption bands in the infrared or in the ultraviolet which allow them to be detected specifically, i.e. to be recognized. This specific detection cooperates with the specific capture performed by the ligands, and reinforces it by superposing one specificity on top of the other.

Chemical or biological species or nanoparticles may be detected/assayed directly by capturing the species to be detected/assayed, or indirectly by replacing or removing a species captured previously by the ligands.

To facilitate applications to the detection of chemical or biological species, including nanoparticles, the carrier may advantageously constitute the bottom of a Petri dish or else of a fluidic cell comprising one or more channels having a minimum diameter of 1 micron, allowing the analyzed gases or liquids to be handled economically and in a perfectly controlled manner.

Figure 4A:
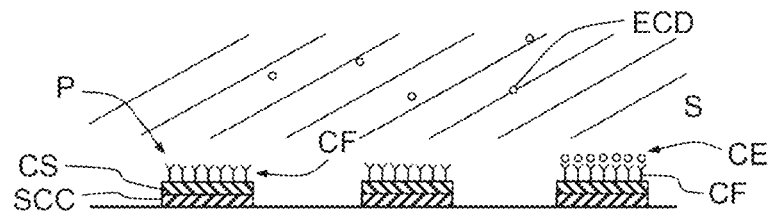
FIGS. 4A to 4E show various embodiments of the invention.

FIG. 4A illustrates one embodiment wherein both the contrast sublayer and the sensitive layer are discontinuous and form pads P. A functionalized layer CF is deposited on the sensitive layer of each pad; typically, different pads receive different functionalizations allowing the selective binding of different chemical or biological species. The functionalized layers are brought into contact with a solution S, for example an aqueous solution, or else with a gas, containing the one or more chemical or biological species to be detected ECD. These species are bound by the functionalized layers of the respective pads and form additional thin films CE, constituting the sample to be observed (the case of a single pad is shown). By observing the biochip under a microscope, under the conditions described above, it is easily possible to identify the species that are actually present in the solution.

Figure 4B:
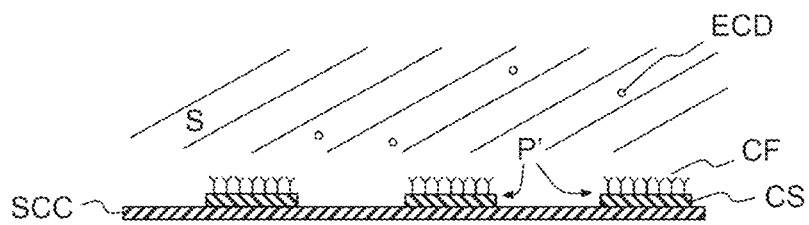

FIG. 4B illustrates one variant wherein the contrast sublayer is continuous, and the pads P' are formed by a discontinuous sensitive layer CS.

Figure 4C:
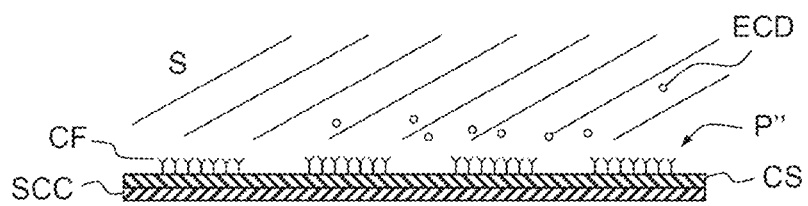

FIG. 4C illustrates another variant wherein both the contrast sublayer and the sensitive layer are continuous, and the pads P''' are defined solely by localized functionalization layers CF. In this case it may be advantageous to provide, outside the pads, a passivation layer preventing the binding of any chemical or biological species contained in said solution ("chemical passivation"). It is possible to use for example a polyethylene glycol, a fluoropolymer, or a fluorinated alkyl.

Figure 4D:
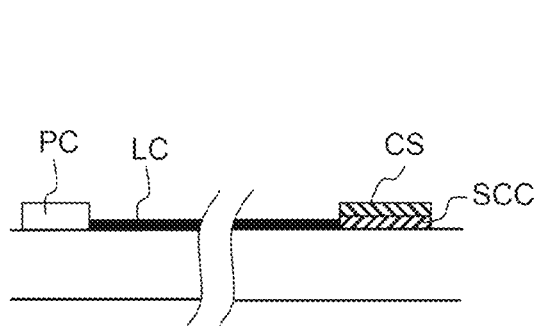
Figure 4E:
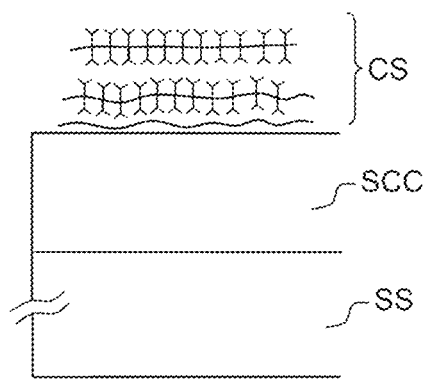

FIG. 4D schematically illustrates the case in which the contrast sublayer is made of metal (or more generally is conductive) and is connected via a conductive line LC to a contact pad PC allowing a voltage to be applied, for example to activate/deactivate in a selective manner the ligands of a functionalization layer or to promote/discourage the capture of a charged target by electrostatic or electrokinetic action (such as electrophoresis). The electroactivation of ligands is described, for example, in the article by Lucian-Gabriel Zamfir et al. "Synthesis and electroactivated addressing of ferrocenyl and azido-modified stem-loop oligonucleotides on an integrated electrochemical device" Electrochimica Acta 164 (2015) 62-70.

FIG. 4B schematically illustrates a sensitive layer CS formed of three sheets of a graphene-type material, two of which exhibit a functionalization on both of their faces. To achieve this, the graphene oxide may be functionalized in solution, then deposited by applying the bubbling method a number times. Under these conditions, an intercalation phenomenon occurs which augments the effectiveness of capture of the species to be detected by the ligands. Detection sensitivity is greatly increased thereby.

The invention claimed is:

1. A contrast-amplifying carrier for observing a sample, comprising a transparent substrate bearing at least one absorbent coating suitable for behaving as an antireflection coating suppressing reflection through destructive interference when it is illuminated at normal incidence at an illumination wavelength $\lambda$ through said substrate and when the face of said coating opposite said substrate is in contact with a transparent ambient medium, a refractive index $n_3$ of which is lower than that of a refractive index $n_0$ of said substrate, wherein said absorbent coating comprises:

a contrast sublayer that is absorbent at said illumination wavelength $\lambda$ and which exhibits an antireflection behavior at said wavelength, deposited on a surface of said transparent substrate; and an absorbent layer, being a sensitive layer, distinct from said contrast sublayer and comprising between 1 and 5 sheets of at least one two-dimensional material, each sheet having a monoatomic or mono-molecular thickness, wherein, a thickness $e_1$ of the contrast sublayer is expressed as a dimensionless parameter $\delta_1$ which equals $2\pi n_0 * e_1/\lambda$, for said illumination wavelength $\lambda$, and for said refractive index $n_0$ of the substrate, said contrast sublayer having a complex index of refraction $N_1 = n_1 - jk_1$, having a real part $n_1$ and an imaginary part $k_1$, the thickness $e_1$ of the contrast sublayer is a first thickness wherein dimensionless parameter $\delta_1$ meets the following conditions:

$$\delta_1 \cong \frac{\left(\frac{n_0}{n_3}-1\right)}{2v_1\kappa_1}\left[1-e^{-\frac{\kappa_1}{K}}\right]$$

where:

$$v_1 = \frac{n_1}{\sqrt{n_0 n_3}};$$

$$\kappa_1 = \frac{k_1}{\sqrt{n_0 n_3}}; \text{ and}$$

$$K = \left\{[\pi/(n_0/n_3 - 1)]\sqrt{n_0/n_3}\right\}^{-1},$$

or the thickness $e_1$ of the contrast sublayer is less than said first thickness, where:

$$v_1^2 \neq 1 + \kappa_1^2.$$

2. The contrast-amplifying carrier as claimed in claim 1, wherein said contrast sublayer is chosen from:
a layer of impurities implanted into said substrate;
a metal layer or made of gold;
a semiconductor layer;
a metal/semiconductor composite alloy;
a magnetic absorbent layer;
a layer of metal nanoparticles;
a nonmetal conductive layer;
a scattering layer;
a polymer or photoresist layer containing pigments or dyes;
an inorganic dielectric layer containing color centers;
a composite hybrid layer comprising a continuous phase throughout which nanoparticles are dispersed; and
a multilayer structure.

3. The contrast-amplifying carrier as claimed in claim 1, wherein said at least one two-dimensional material is a graphene-type material.

4. The contrast-amplifying carrier as claimed in claim 3, wherein said sensitive layer is chosen from:
a single sheet of a graphene-type material;
a stack of 2 to 5 sheets of at least one graphene-type material;
a single sheet or a stack of 2 to 5 sheets of at least one surface-functionalized graphene-type of material; and
a stack of 2 to 5 sheets of at least one graphene-type material, at least one of which is functionalized on both faces.

5. The contrast-amplifying carrier as claimed in claim 3, wherein the graphene-type material of said sensitive layer is chosen from:
raw graphene;
graphene oxide;
reduced graphene oxide; and
doped graphene.

6. The contrast-amplifying carrier as claimed in claim 1, wherein said absorbent coating is discontinuous, forming a plurality of pads on the surface of said substrate.

7. The contrast-amplifying carrier as claimed in claim 1, wherein said contrast sublayer is continuous and said sensitive layer is discontinuous, forming a plurality of pads on the surface of said substrate.

8. The contrast-amplifying carrier as claimed in claim 1, wherein said sublayer is conductive and is linked by a conductive line to a contact pad allowing the application of an electrical potential.

9. The contrast-amplifying carrier as claimed in claim 1, wherein said antireflection absorbent coating exhibits, at normal incidence, a transmittance higher than or equal to 80%, or higher than or equal to 85% or higher than or equal to 90% at said wavelength $\lambda$.

10. The contrast-amplifying carrier as claimed in claim 1, wherein said antireflection absorbent coating exhibits, at normal incidence, at said wavelength $\lambda$, a reflectivity lower than or equal to 1%, or lower than or equal to 0.5% or lower than or equal to 0.1% or lower than or equal to 0.05%.

11. The contrast-amplifying carrier as claimed in claim 1, wherein said sensitive layer is functionalized by the addition or the natural presence of ligands that are capable of binding at least one chemical or biological species.

12. The contrast-amplifying carrier as claimed in claim 11, forming the bottom of a Petri dish or of a fluidic cell.

13. The contrast-amplifying carrier as claimed in claim 1, wherein $k_1 \geq 0.01$.

14. The contrast-amplifying carrier as claimed in claim 1, wherein $k_1 \geq 0.15$.

15. A method for observing a sample including the following steps:

A. placing said sample on the sensitive layer of a contrast-amplifying carrier as claimed in claim 1 and bringing it into contact with a transparent ambient medium, the refractive index of which is lower than that of the substrate of said contrast-amplifying carrier;

B. illuminating said sample at normal incidence through said ambient medium, with an illumination cone including the normal incidence, with light radiation including at least one wavelength λ such that the absorbent coating of said carrier behaves as an antireflection coating; and C. observing the sample thus illuminated, also through said ambient medium.

16. The method as claimed in claim 15, wherein said step C. is carried out by detecting fluorescence radiation or Raman scattering.

17. A method for detecting or assaying at least one chemical or biological species or nanoparticles including the following steps:
  I. providing a contrast-amplifying carrier as claimed in claim 14, comprising a functionalized sensitive layer that is capable of binding at least one chemical or biological species or nanoparticles;
  II. bringing said functionalized surface or layer into contact with at least one solution containing a chemical or biological species that is capable of binding to said functionalized surface or layer, said solution being substantially transparent and exhibiting a refractive index that is lower than that of the substrate of said contrast-amplifying carrier;
  III. illuminating said sample at normal incidence through said ambient medium at an illumination wavelength λ such that the absorbent coating of said carrier behaves as an antireflection coating; and
  IV. observing said contrast-amplifying carrier thus illuminated, also through said substrate.

18. The method as claimed in claim 17, wherein said step IV. is carried out by detecting fluorescence radiation or Raman scattering.

* * * * *